(12) United States Patent
Sullivan et al.

(10) Patent No.: US 10,661,025 B2
(45) Date of Patent: May 26, 2020

(54) PEN NEEDLE OUTER COVER CONCEPTS

(71) Applicant: Becton, Dickinson and Company, Franklin Lakes, NJ (US)

(72) Inventors: Sean Sullivan, Ridgewood, NJ (US); Sudarsan Srinivasan, Hawthorne, NJ (US); Michael DiBiasi, Pompton Plains, NJ (US); Keith Knapp, Warwick, NY (US); Kunjal Oza, North Brunswick, NJ (US); Sajayesh Vijayachandran, Kannur (IN); Ganesh Kamble, Pune (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 656 days.

(21) Appl. No.: 15/100,279

(22) PCT Filed: Dec. 4, 2014

(86) PCT No.: PCT/US2014/068567
§ 371 (c)(1),
(2) Date: May 27, 2016

(87) PCT Pub. No.: WO2015/085068
PCT Pub. Date: Jun. 11, 2015

(65) Prior Publication Data
US 2017/0034697 A1    Feb. 2, 2017

Related U.S. Application Data

(60) Provisional application No. 61/912,538, filed on Dec. 5, 2013.

(51) Int. Cl.
*A61M 5/00*     (2006.01)
*A61M 5/32*     (2006.01)
(Continued)

(52) U.S. Cl.
CPC .......... *A61M 5/3213* (2013.01); *A61M 5/002* (2013.01); *A61M 5/3202* (2013.01);
(Continued)

(58) Field of Classification Search
CPC .............. A61M 5/3202; A61M 5/3293; A61M 5/3213; A61M 5/002; A61M 2005/3254
See application file for complete search history.

(56) References Cited

U.S. PATENT DOCUMENTS

2006/0032769 A1    2/2006  Erickson et al.
2009/0069753 A1*   3/2009  Ruan .................... A61M 5/3202
                                                         604/192

(Continued)

FOREIGN PATENT DOCUMENTS

JP    H10113389       5/1998
JP    2003199731      7/2003
(Continued)

*Primary Examiner* — Nathan R Price
*Assistant Examiner* — Anh Bui
(74) *Attorney, Agent, or Firm* — Dickinson Wright PLLC

(57) ABSTRACT

A pen needle is enclosed by an outer cover to facilitate installation of a needle bearing hub on a medication pen. The outer cover design reduces or eliminates the likelihood of user contact with the patient end needle or the non-patient end needle during installation and disposal, and provides an audible indication when the hub is fully installed on a medication pen.

13 Claims, 9 Drawing Sheets

(51) Int. Cl.
*A61M 5/50* (2006.01)
*G06F 9/4401* (2018.01)
*H04L 29/06* (2006.01)

(52) U.S. Cl.
CPC ........ *A61M 5/3205* (2013.01); *A61M 5/3293* (2013.01); *A61M 5/50* (2013.01); *A61M 5/5086* (2013.01); *G06F 9/4416* (2013.01); *H04L 63/0876* (2013.01); *A61M 2005/3254* (2013.01)

(56) References Cited

U.S. PATENT DOCUMENTS

| | | | | |
|---|---|---|---|---|
| 2009/0069755 A1* | 3/2009 | Horvath | ............... | A61M 5/3293 604/240 |
| 2012/0016300 A1* | 1/2012 | Ruan | ..................... | A61M 5/002 604/110 |
| 2012/0123334 A1* | 5/2012 | Schraga | .............. | A61M 5/3202 604/111 |
| 2012/0165745 A1* | 6/2012 | Nielsen | ................ | A61M 5/3202 604/192 |
| 2013/0105345 A1* | 5/2013 | Van der Beek | ....... | A61M 5/002 206/366 |

FOREIGN PATENT DOCUMENTS

| | | |
|---|---|---|
| JP | 2009101140 A | 5/2009 |
| WO | WO-2014105905 A2 | 7/2014 |

* cited by examiner

PEN NEEDLE OUTER COVER CONCEPTS

CROSS REFERENCE TO RELATED APPLICATIONS

This application claims the benefit of U.S. Provisional Patent Application No. 61/912,538, filed Dec. 5, 2013, which is incorporated by reference.

BACKGROUND OF THE INVENTION

Field of the Invention

The invention is the field of medication delivery devices, and in particular, the invention is directed to medication pens, and specifically, a pen needle having an outer cover that facilitates installation of the pen needle on a medication pen body and subsequent removal of the pen needle after use with simultaneous protection of the non-patient end cannula.

Description of the Related Art

Pen needles are widely used in medication delivery systems for self-administered injectable drugs. In one popular arrangement, the pen needle is provided in an outer cap which is sealed with a layered paper and foil "teardrop label." The user removes the heat sealed tear-drop label from the outer cap to expose the proximal or "non-patient' end needle located in a cavity on the proximal end of the needle-bearing hub. The exposed needle-bearing hub is then threaded onto a medication pen such that the non-patient end of the needle pierces the closure of the drug storage compartment of the medication pen. The cap is removed, and a smaller needle shield, which slides over a post on the hub supporting the patient-end needle, is also removed prior to performing an injection. The cap may also be used to remove the needle-hub assembly. Although this system has garnered public acceptance, it is nevertheless desirable to enhance ease of use.

SUMMARY OF THE INVENTION

To avoid difficulty aligning the non-patient end needle with the medication pen to thread the pen needle on the pen, one object of the invention is to provide a pen needle that self-aligns on the medication pen during installation. Another object of the invention is to provide a cover over the non-patient end needle that may be re-closed after use or after opening but prior to installation on the pen.

According to one embodiment of the invention, the foregoing objectives are achieved using a pen needle comprising: an outer cover having a closed distal end with gently concave sides affording a finger hold and an open proximal end receiving a needle-bearing hub. The needle bearing hub according to this embodiment has an open proximal end defined by a proximal edge aligned with the open proximal end of the outer cover in the initial state. A flap hinged to the proximal edge of the hub (or to the open end of the outer cover) has an open position permitting installation of the hub on the medication pen and a closed position enclosing the non-patient end of the needle within the hub (or within the outer cover).

The outer cover in this embodiment may be provided with a cut out defining a flexible strip in a sidewall of the outer cover inboard of the open proximal end. A radially inward facing projection on the strip engages contours on a radially outward surface of the hub, so that when the outer cover is rotated with respect to the hub the projection generates an audible sound or tactile sensation as the projection on the strip snaps against the contours on the hub. In some embodiments, the strip is oriented circumferentially and acts as a pawl mechanism, resisting rotation in the counterclockwise direction.

In another embodiment according to the invention, a pen needle is provided with an outer cover having a closed distal end with tapered sides affording a finger hold and an open proximal end receiving a needle-bearing hub. The hub has longitudinal cutouts extending to the proximal edge of the outer cover defining a plurality of projections extending proximally from the proximal open end and curved radially outwardly from the hub. In the initial state, with the needle-bearing hub contained in the outer cover, the projections extend beyond the proximal end of the hub and flex slightly inward to protect the user from needle stick from the non-patient end needle. Thus, in this embodiment, projections flex outwardly to release the needle bearing hub during installation and flex inwardly to contain the needle bearing hub for storage.

As in the previous embodiment, a flexible strip may be formed in a sidewall of the outer cover, provided inboard of the open proximal end, with an inward-facing projection on the strip engaging contours on a radially outward surface of the hub, so that when the outer cover is rotated with respect to the hub, the projection provides sensory feedback as it contacts the contours on the hub surface. The strip is oriented circumferentially, so that it acts as a pawl mechanism, resisting rotation in the counterclockwise direction.

In another aspect, the invention is directed to a pen needle outer cover with an extended proximal end side wall, such that the outer cover side wall on the proximal end extends beyond the end of the non-patient end needle. Therefore, the needle is recessed in a cavity on the proximal end of the pen needle and the hub cannot be mated with the medication pen until the needle is axially aligned with the medication pen. This arrangement ensures that the hub is self-aligned with the medication pen, and that the non-patient end needle is always in the proper axial orientation with respect to the medication pen before the hub is mated onto the medication pen.

The figures are schematic for the purpose of illustrating the invention and not drawn to scale. Features may be enlarged, made smaller, simplified, or eliminated to show how the parts operate according to the invention.

DETAILED DESCRIPTION OF THE INVENTION

As used herein, the "distal" direction is in the direction of the injection site, and the "proximal direction" is the opposite direction. The "axial" direction is along the longitudinal axis of the injection device and a "diameter" is generally a diameter with respect to a longitudinal axis. The cannula is generally arranged axially in the device. "Radially" is a direction perpendicular to the axial direction. Thus, "radially inward" generally means closer to the needle. An element extending in the "circumferential direction" means that the element extends around the circumference; for example threads on a medication pen are arranged circumferentially on the distal end of the pen. "Medication pen" is used broadly herein to refer to any prefilled medication delivery device. However, in the most preferred embodiments a medication pen is characterized by having a pen-shaped body and a proximally located thumb button adapted for automatic dosing. A "cut out" refers to a feature on a surface defined by through openings in the surface (inner and outer sides of the surface); a cut-out is said to be "inboard" if the opening(s) do not extend to the edge of the surface.

The pen needles according to the invention are provided with a cover that has tapered sides to facilitate gripping and means to engage the hub in the outer cover so that the two elements rotate together as the hub is installed on a pen needle. The tapered sides are gently concave to conform approximately to a user's fingers to provide a finger hold. In multiple embodiments, the outer cover is provided with a flexing strip which contacts contours on the radially outer surface of the hub to provide an audible indication when the outer cover rotates with respect to the hub after the needle-bearing hub is installed on a medication pen. The strip may have a pawl mechanism so that the outer cover resists rotation with respect to the hub in the counter-clockwise direction when the hub is being removed.

Figure 1:
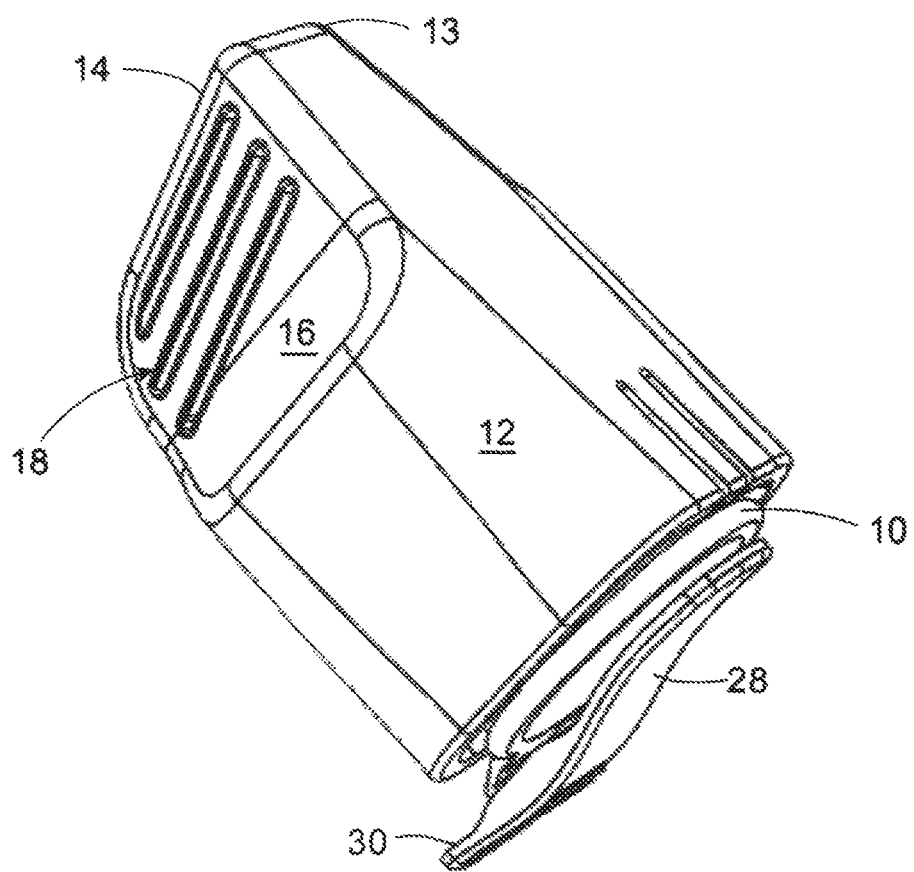
FIG. 1 depicts an outer cover and hub assembly according to an embodiment of the invention.
Figure 2:
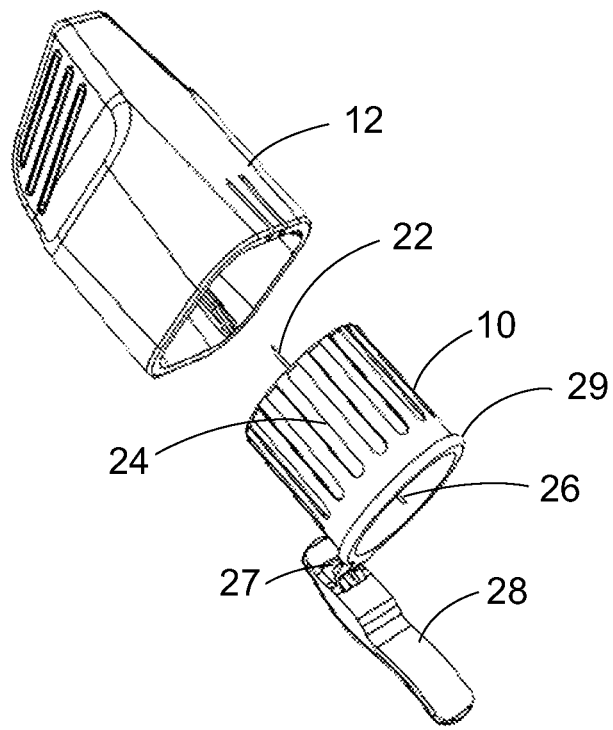
FIG. 2 depicts the outer cover and hub assembly of FIG. 1 in an exploded view.

In the embodiment of FIG. 1, outer cover 12 has closed distal end 14 formed by concave tapered sides 16 terminating at corners 13. A side of the closed distal end opposite the corners is rounded. The tapered sides 16 prompt and facilitate gripping with the thumb and index finger, and may be provided with ribs 18 for this purpose. Sides 16 are described as "gently concave" which is intended to convey that they are shaped to hold with the fingers. Hub 10 is received in the proximal end of the outer cover 12. The exploded view of FIG. 2 shows the orientation of the hub 10 as it fits in the outer cover 12, such that the patient end needle 22 projects from the patient-facing surface of hub 10 into the inside of outer cover 12. The open end of needle-bearing hub 10 is adapted to be attached to a medication pen. Typically, the hub is adapted with threads, mating with corresponding threads on the medication pen. However, the hub may be adapted with one or more groove(s) and/or protuberance(s) mating with a corresponding groove(s) and/or protuberance(s) on the medication pen allowing the hub to be installed, with or without rotation, and snapped in place. A friction fit between the hub and medication pen may also be employed. The attachment means are left to the skill of the artisan to select. Proximal edge 29 defining the open end of hub 10 is aligned with the open end of the hub cover 12 in the assembled state. Non-patient end needle 26 is adapted to pierce the septum of a medication cartridge within a medication pen body when the hub is installed, and preferably needle 26 does not project beyond the plane formed by proximal edge 29 of the opening of hub 10. Typically, the patient end needle and the non-patient end needle are opposite ends of a single stainless steel cannula which is beveled to a point on each end and is affixed in an axial bore in the hub by adhesive or other means. Reference to a "patient end needle" and a "non-patient end needle" refers to the needle points—typically (but not necessarily) they are opposite ends of the same cannula.

In the embodiment depicted, guard flap 28 is attached to proximal edge 29 of hub 10 by hinge 27 which is capable of maintaining at least two positions: a first open position for installing the hub and a second closed position for transporting the hub or discarding after use. In the closed position, shown in FIG. 1, flap 28 shields the non-patient end needle 26 from accidental needle stick. In the open state shown in FIG. 2, non-patient end needle 26 is exposed, the flap 28 is parallel with the axis of the needle, and the hub can be threaded onto a medication delivery device. Plastic camming and locking elements (not shown) may be provided on the hinge, bearing against the hub or outer cover to retain the flap in the first or second position and providing resistance when the flap is moved from the first to the second position or from the second position to the first. Various hinge constructions are known in the art which can be adapted for use with injection molded parts, such as a one-piece living hinge, which may be molded with hub 10, including flap 28 in the same process. Hinges, including camming elements and locking fixtures, are disclosed, for example, in U.S. Pat. No. 8,887,912, which is incorporated by reference for this purpose. The hinge design may be left to the person of ordinary skill in the art. In embodiments, flap 28 may be hinged to outer cover 12 instead of the hub.

In embodiments, flap 28 may be provided with two closed positions: a first closed position where the flap is held releasably (against the resistance of a camming surface, for example), which allows the hub to be transported and later opened, so that the needle-bearing hub can be installed on a medication pen; and a second position in which the flap is permanently locked in the closed position for disposal. As shown in FIG. 1, a portion 30 of the flap 28 may project outwardly beyond an outer periphery of the outer cover 12 in the first and/or second closed position.

Figure 3:
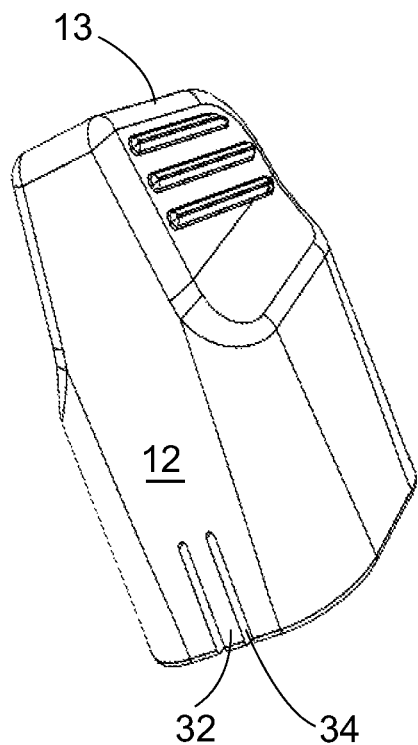
FIG. 3 depicts a perspective view of an outer cover according to an embodiment of the invention.
Figure 4:
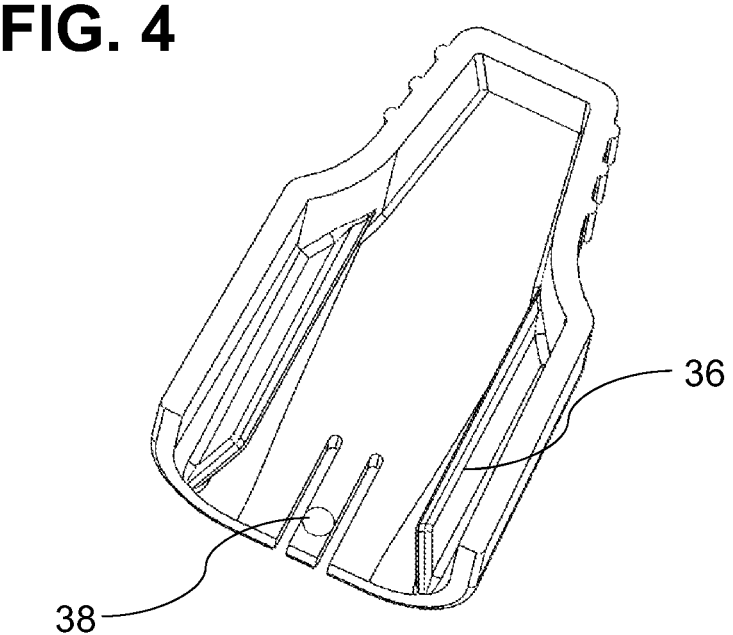
FIG. 4 is a cutaway view of the interior of the outer cover of FIG. 3.
Figure 9:
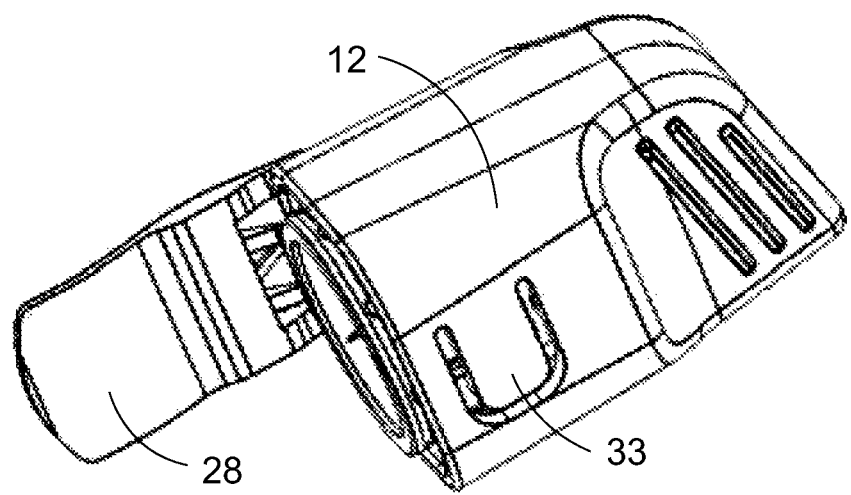
FIG. 9 is a view of the outer cover and hub assembly of FIG. 1 in the open position.

In the embodiment shown in FIG. 9, outer surface of hub 10 is preferably provided with a series of longitudinally arranged grooves 24 which cooperate with a strip 33 formed on outer cover 12 to provide an audible indication when the hub is fully installed on the medication pen. In the embodiment shown in FIG. 3, strip 32 is formed between cuts 34 formed at the open proximal end of the outer cover 12 such that the strip 32 can be flexed with respect to the outer cover 12. As shown in the interior cutaway view of FIG. 4, the inside of the outer cover 12 includes a projection 38 formed on a radially inward surface of the strip 32. A similar projection (not shown) may be provided on a radially inward surface of strip 33 in the embodiment of FIG. 9. In the case where the hub is attached to the medication pen by rotating the hub onto a threaded connection, the hub and outer cover initially rotate in unison. This may be ensured by providing an interference fit between hub 10 and outer cover 12.

Optionally, longitudinal ribs 36 on an interior surface of outer cover 12 engage hub 10 to provide the interference fit. However, once hub 10 is fully threaded onto the medication pen, turning the outer cover further causes the outer cover 12 to rotate with respect to the hub. Flexible strip 32 flexes as the projection 38 is dragged across the grooves 24 making an audible ratchet sound and/or providing a tactile sensation which indicates that the hub is fully installed on the medication pen.

In FIG. 9, strip 33 is oriented circumferentially on the outer cover inboard of the open proximal end, so that strip 33 acts as a pawl mechanism. In this configuration an inward facing projection on strip 33 (not shown in FIG. 9) is dragged across contours 24 on the hub when the outer cover is rotated in a clockwise direction after the hub is fully seated on a medication pen, but reversing the direction causes outer cover 12 and hub 10 to rotate together when hub 10 is uninstalled from the medication pen for disposal.

Figure 5:
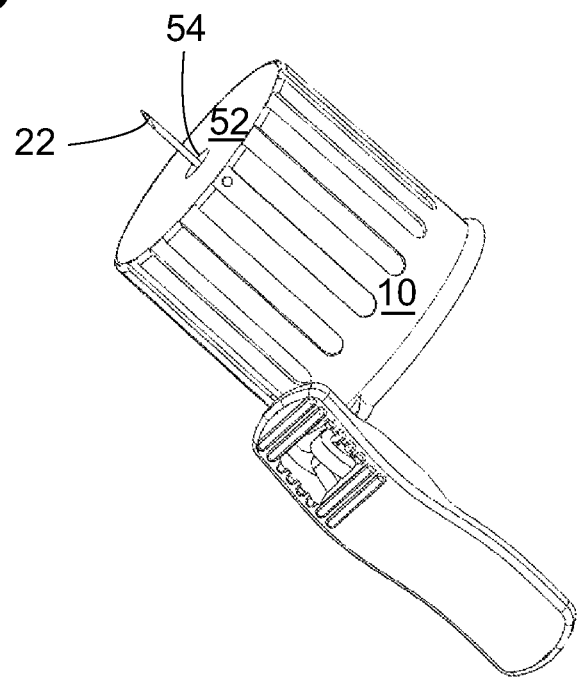
FIG. 5 is a perspective view of a hub assembly according to an embodiment of the invention.
Figure 7:
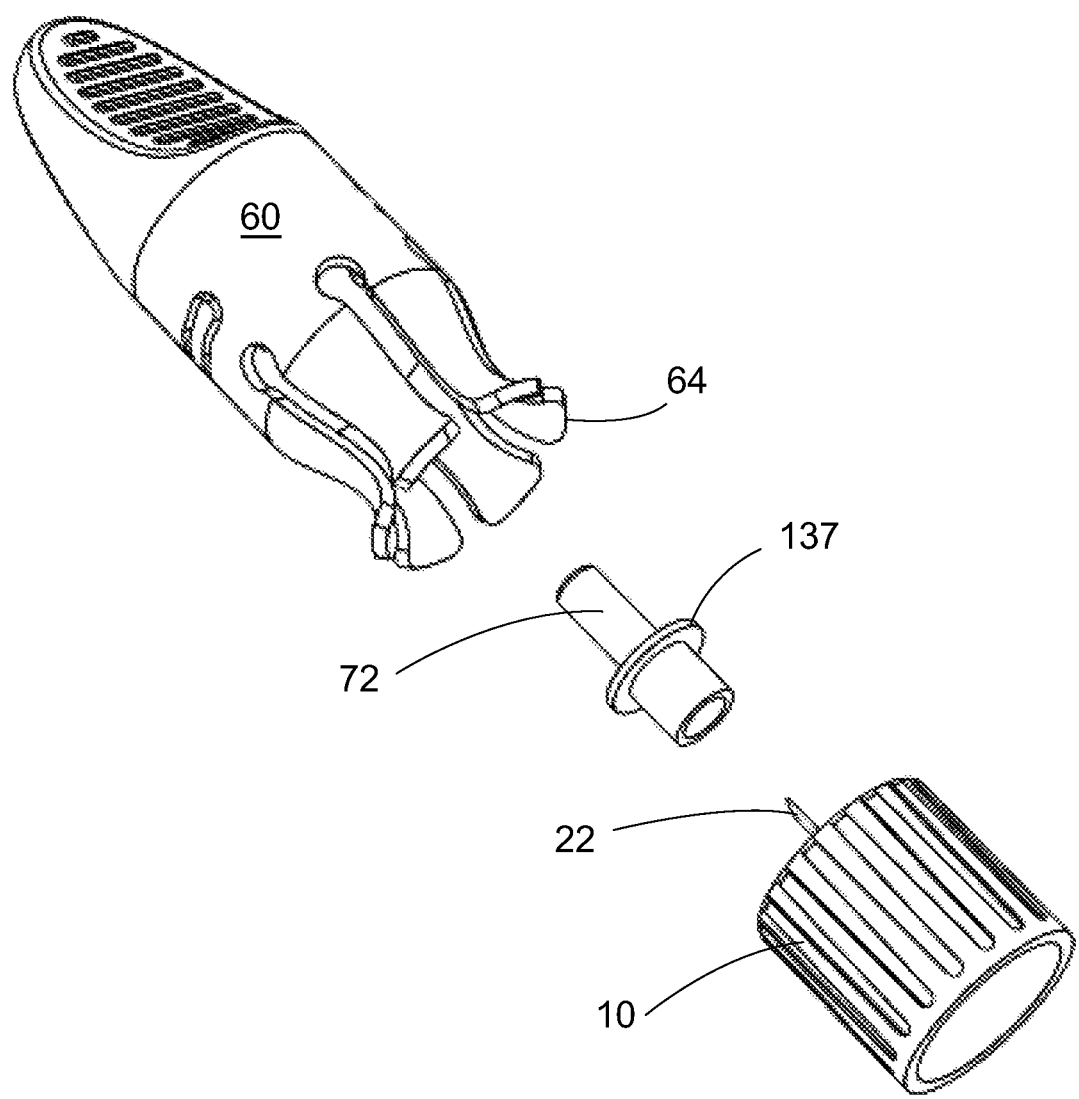
FIG. 7 is an exploded view of the assembly of FIG. 6.
Figure 8:
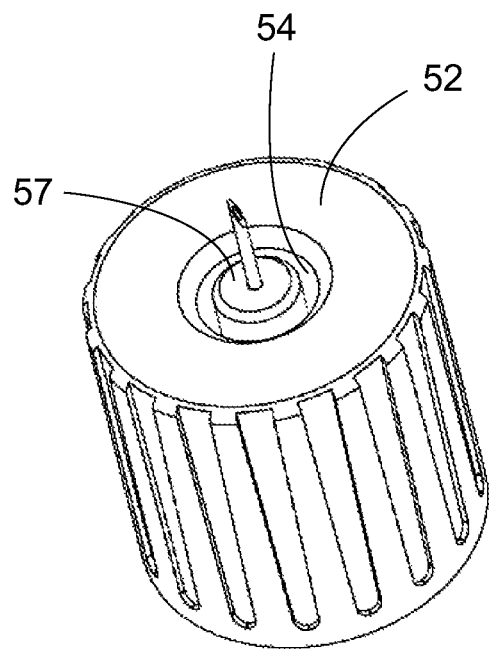
FIG. 8 is a view of the needle-bearing hub according to one embodiment of the invention, showing the distal patient-facing side with a slot for receiving an inner needle shield.

Distal face 52 of needle-bearing hub 10 according to different embodiments of the invention is shown in FIG. 5 and FIG. 8. As seen in FIG. 5 and FIG. 8, distal face 52 of hub 10 is predominately flat, from the needle to the periphery of the hub, except for an annular channel 54 around the needle. A needle bearing post is recessed in the hub and the annular channel 54 is formed radially around patient end needle 22. This annular channel 54 receives an inner needle shield 72 which is provided with flange 137 (inner shield 72 including flange 137 may be substantially identical to the embodiment shown in FIG. 7) to situate the inner shield 72 in the annular channel 54. A hub with a flat pressure pad area is disclosed in U.S. Patent Application Publication No. 2009/0069755, which is incorporated by reference in its entirety for this purpose.

To install a needle bearing hub 10 onto a medication pen using the outer cover of FIG. 1, flap 28 is opened from the closed position shown in FIG. 1, until it aligns with the longitudinal axis of the pen needle, in the position shown in FIG. 9. In this state, the user holds the hub by outer cover 12 and installs internally threaded hub 10 on a medication pen by rotating the assembly clockwise onto the threaded end of the pen. At a certain point, when hub 10 is fully seated, outer cover 12 rotates with respect to hub 10 after the hub has been fully installed, and the projection on strip 33 makes a ratchet sound as it drags across the grooves 24 on the hub. The outer cover is removed by pulling distally, leaving the hub secured on the medication pen. In this state, the medication pen is readied for administering an injection. The outer cover is replaced and turned counterclockwise to remove the hub from the pen. Flap 28 may thereafter be closed to prevent accidental needle stick during disposal.

Figure 6:
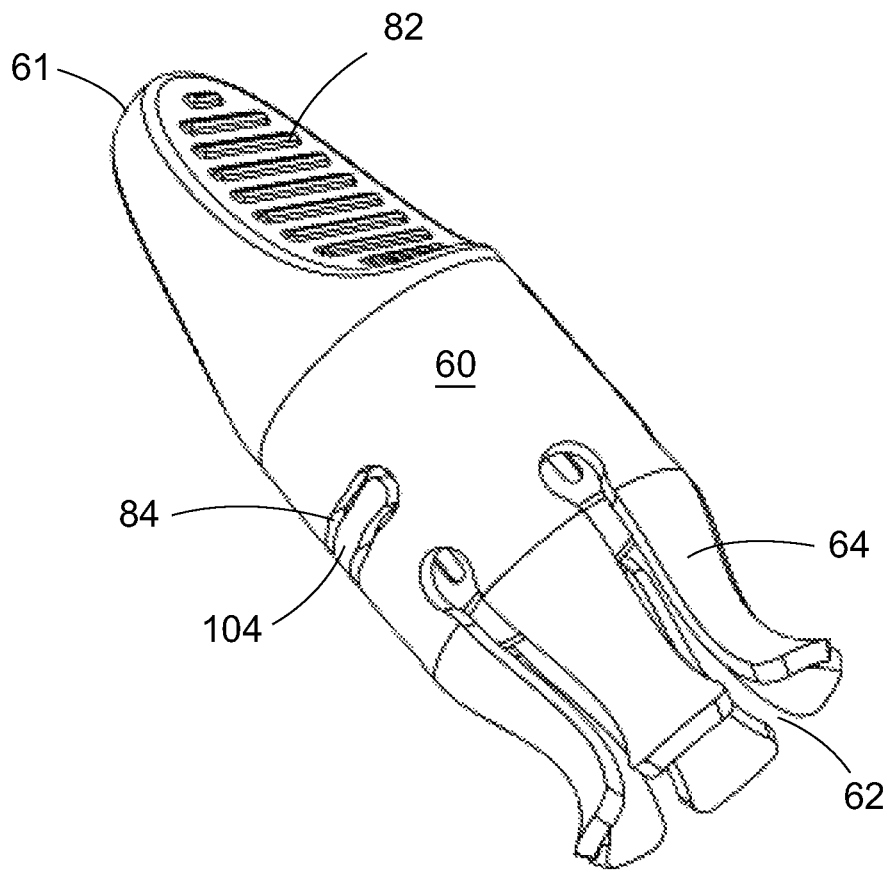
FIG. 6 is a perspective view of an outer cover according to another embodiment of the invention.

FIG. 6 depicts another embodiment of the invention wherein the open proximal end of outer cover 60 assists in grasping the pen needle. Outer cover 60 has tapered sides adapted to be gripped by thumb and forefinger, meeting at a curved closed distal end 61. The tapered sides are gently concave to provide a finger hold, as in the previous embodiment. The tapered sides on the outer cover may be provided with ribs 82 to enhance the user's finger hold, meeting at a curved distal end, as shown in FIG. 6. The open proximal end is configured with longitudinal cutouts 62 extending to the proximal edge of the outer cover defining a plurality of projections 64 extending proximally and curved radially outwardly from the hub. The projections 64 extend beyond the hub in the proximal direction when the hub is received fully within the outer cover, which protects the user from accidental needle stick from the non-patient end needle. Projections 64 are formed to flex outwardly when cover 60 is pulled off the hub, for example.

The exploded view of FIG. 7 shows hub 10 aligned with inner needle shield 72 in the orientation that these elements are inserted in outer cover 60. As in the previous embodiment and as shown in FIG. 7, the outer radial surface of hub 10 may be provided with contours. As shown in FIG. 6, cutout 84 forms a flap 104 inboard of the open proximal end. The flap is provided with a projection facing radially inward toward the hub (not shown in the Figure). The circumferential orientation of inboard flap 104 acts as a pawl, resisting rotation of the outer cover with respect to the hub in the counterclockwise direction.

Distal patient-facing side 52 of hub 10 according to one embodiment of the invention is shown in FIG. 8. The effective penetration depth of the needle is not critical and may be 4 mm to 8 mm, or other standard length known in the art, or a non-standard length. In the embodiment shown, the hub post 57 bearing the needle is embedded in the hub. Annular slot 54 is provided around the hub post to accommodate inner needle shield 72. Inner needle shield is provided with a flange 137 to fit securely in the annular slot.

The installation sequence for the needle-bearing hub with the outer cover of FIG. 6 is similar to the sequence for the outer cover of FIG. 1. Before use, hub 10 is within outer cover 60 and projections 64 on outer cover 60 extend beyond the distal end of the hub and bend slightly inwardly to protect the user from the non-patient end of the needle on the hub. Pressing outer cover 60 onto the threaded end of a medication pen causes projections 64 to flare outward, which allows medication pen to access hub 10 and for hub 10 to be threaded onto a pen with a clockwise turn of outer cover 60. Turning outer cover 60 beyond the point at which the hub is fully installed on the pen, causes outer cover 60 to rotate with respect to hub 10, creating an audible and/or tactile indication as the flexible strip 104 on the sidewall of the outer cover drags across the contoured surface of hub 10. At this point, outer cover 60 can be removed by pulling it in the distal direction. The user removes inner shield 72 covering the needle and the pen is injection-ready. To remove and store hub 10 for disposal, cover 60 is placed proximally over the hub, rotated counter-clockwise, and pulled distally with hub 10 substantially enclosed within projections 64 of the outer cover.

Figure 10:
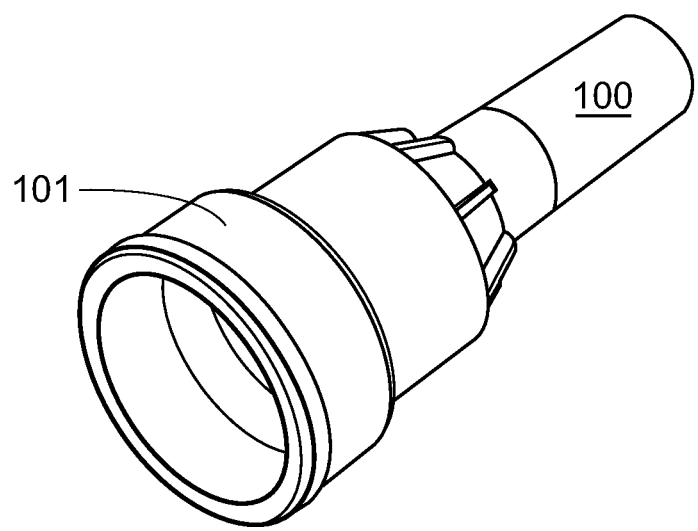
FIG. 10 is a pen needle outer cover having an extended side wall.
Figure 11:
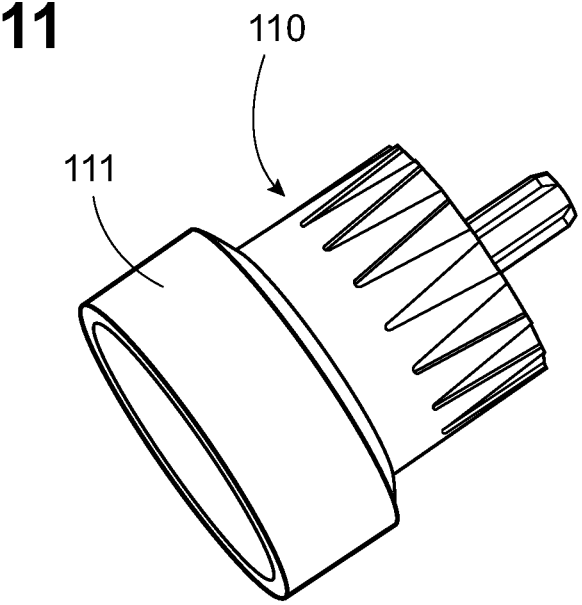
FIG. 11 is hub adapted to be received in the pen needle outer cover of FIG. 10.
Figure 12:
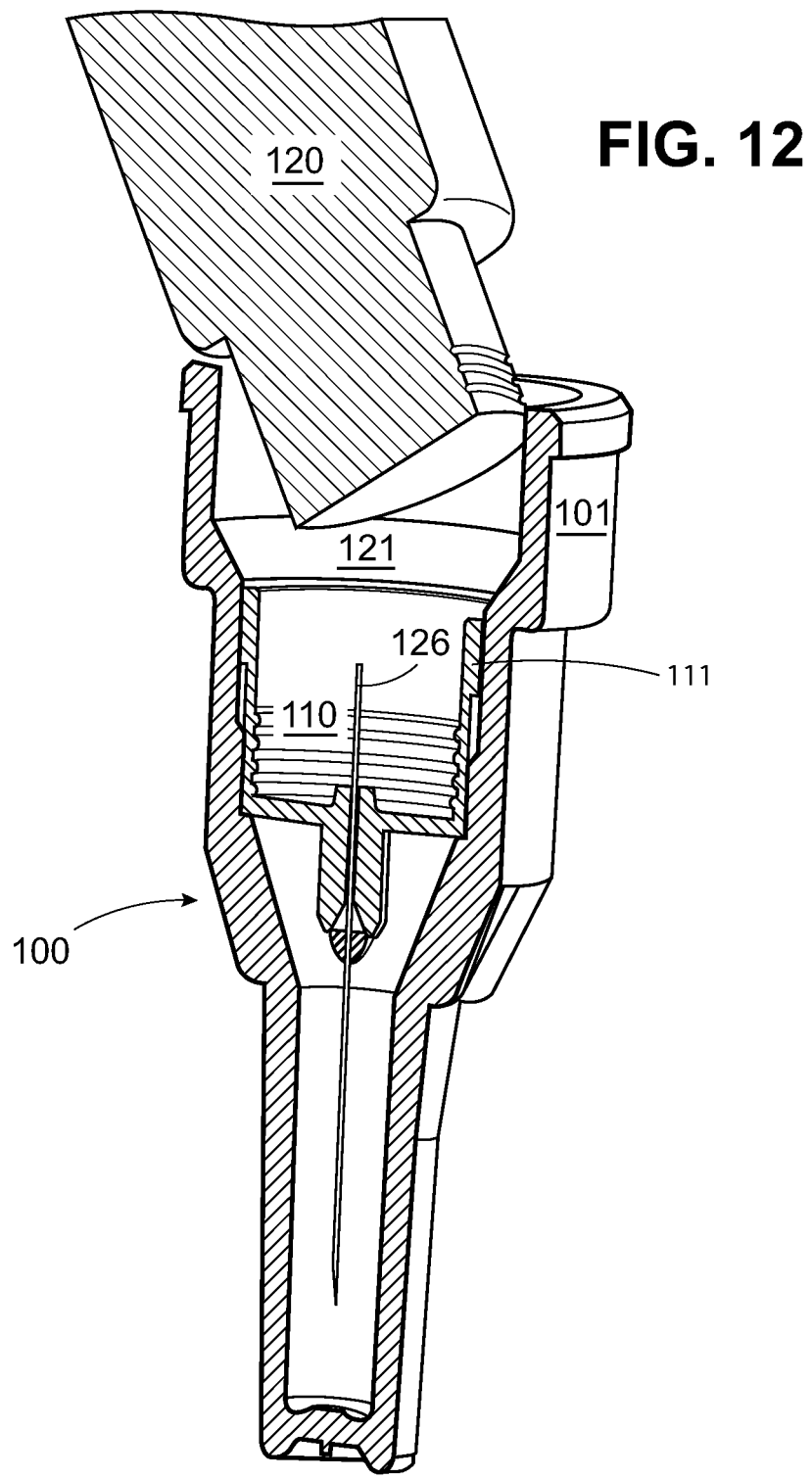
FIG. 12 shows the engagement of a medication pen with a hub according to FIG. 11 received in pen needle outer cover according to FIG. 10.
Figure 13:
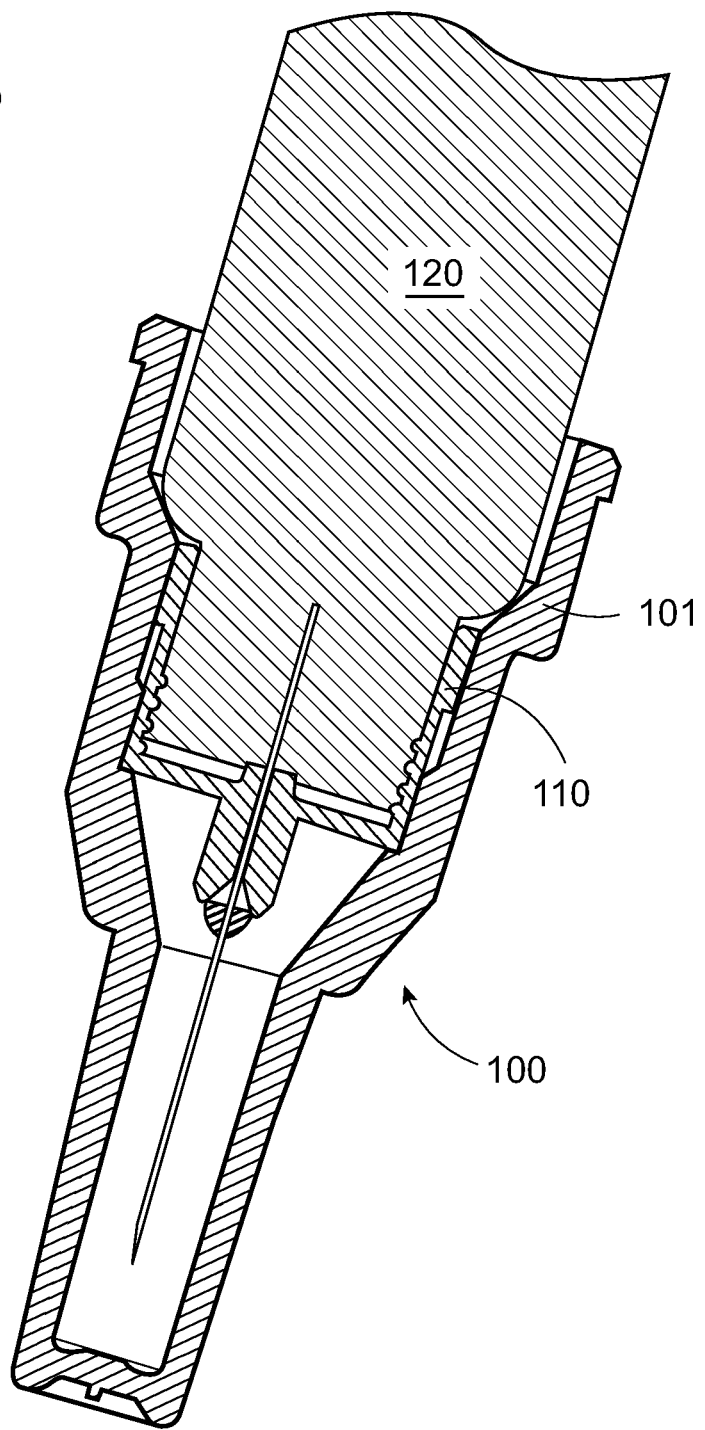
FIG. 13 shows the assembly of FIG. 12 with the hub seated on the medication pen.

A further aspect of the invention is depicted in FIG. 10 through FIG. 13. In FIG. 10, outer cover 100 is provided with an extended proximal side wall 101 extending beyond the tip of non-patient end needle 126 when hub 110 is received in outer cover 100. FIG. 11 depicts hub 110, which, in this embodiment, is likewise provided with an extension 111 beyond proximal end of non-patient end needle 126. Extended side wall 101 prevents inadvertent contact of medication pen 120 with non-patient end needle 126. As shown in FIG. 12 and FIG. 13, the extended flange features 101, 111 are provided so that cover 100 and hub 110, assembled together, self-align when installed on medication pen 120. Some clearance is provided between cover 100 and medication pen 120 to permit hub 110 to be installed on medication pen 120, by threading or the like. Therefore, the diameter of the proximal end side wall of the outer cover is larger than the diameter of the proximal end of the hub.

In order to prevent non-patient end needle 126 from entering medication pen 120 at an angle, bending, and possibly failing to reach medication in a medication compartment therein, extended side wall 101 orients the medication pen as it is inserted in the opening. Any extension of the outer cover in the proximal direction beyond the proximal end of the hub will assist in guiding outer cover 100, and therefore hub 110, onto a medication pen. For example, an extended side wall of 0.01 inch to 1.00 inch is operable. Preferably the side wall extends about 0.20 inch to about 1.00 inch beyond the needle, and more preferably the extended flange has a length of about 0.25 inch to about 0.50 inch beyond the proximal end of the non-patient end needle. These dimensions apply to the proximal end flange portions of cover 101 and proximal end flange portion of hub 111. Sloped sides 121 on an internal surface of cover 100 between proximal end sidewall 101 and a distal portion of cover 100 guide medication pen 120 into place irrespective of the angle at which the user initially places the assembly on medication pen 120. Where hub 110 is provided with extended proximal end sidewall 111, engagement of hub extended sidewall 111 and outer cover extended sidewall 101 prevents hub 110 from moving during installation on a medication pen. Alternatively, or in addition, for this purpose, a friction fit may be provided between hub 110 and cover 100, for example using sloped inward projecting ribs on cover 100 which fit against hub 110. Alternatively a locking feature such as a protuberance or groove on hub 110 may cooperate with a cooperating feature on outer cover 100 to retain hub 110 in place during installation. A locking feature, if used, may be overcome by pulling the outer cover distally from the hub after installation.

Cover 100 may be made transparent so a user can view the status of the medication in pen 120. The installed state is depicted in FIG. 13.

The plastic parts described herein, including the hub and outer cover in all the embodiments, are made of polymers suitable for injection molding, including without limitation, polypropylene and others known in the art. Likewise, techniques for injection molding, draw molding and the like, are well known to those having skill in the art of manufacturing medication pens. However, the invention is not limited to any particular production method. The needle is typically a standard gauge surgical stainless steel part. Pen needles according to the invention are designed to be user-friendly, adapted for self-administered medications, such as insulin, but the invention is not limited to any particular medication. Likewise, although the 4 mm-8 mm injection depth needle described above is suited for subcutaneous injection, the invention may also be adapted for use with intradermal injection.

The foregoing description of the preferred embodiments is not to be deemed to limit the invention, which is defined by the following claims. The different embodiments are related, such that features recited in the dependent claims are capable of combination with each other, with other independent claims, and with other embodiments.

The invention claimed is:

1. A pen needle, comprising:
   an outer cover having a closed distal end with gently concave sides forming a finger hold and an open proximal end receiving a needle-bearing hub having a patient end needle and a non-patient-end needle;
   the needle bearing hub having an open proximal end adapted to be attached to a medication pen, the open proximal end of the hub being defined by a proximal edge aligned with the open proximal end of the outer cover in an initial state prior to installation of the hub on the medication pen; and
   a flap attached to the proximal end of the outer cover by a hinge having camming or locking elements for maintaining the flap in an open position permitting installation of the hub on the medication pen and in a first closed position enclosing the non-patient end of the needle within the hub or outer cover; wherein
   the flap is releasably held in the first closed position, which allows the hub to be transported and the flap later opened, so that the hub can be installed on the medication pen; and
   the flap is movable to a second closed position in which the flap is permanently locked for disposal.

2. The pen needle according to claim 1, wherein the patient end needle and the non-patient end needle are opposite ends of a single cannula received in an axial bore in the needle bearing hub.

3. The pen needle according to claim 1, further comprising an annular slot formed in a distal patient-facing surface of the hub, said slot receiving an inner needle shield having a closed distal end covering the patient-end needle, an open end received in the annular slot, and a flange between the open end and the closed distal end positioning the inner needle shield in the annular slot.

4. The pen needle according to claim 1, further comprising
   a cut out defining a flexible strip in a sidewall of the outer cover inboard of the open proximal end; and
   a projection formed on a radially inward surface of the strip engaging contours on a radially outward surface of the hub so that when the outer cover is rotated with respect to the hub the projection provides sensory feedback to the user by snapping against the hub outer surface.

5. The pen needle according to claim 4, wherein the flexible strip is circumferentially arranged on the outer cover sidewall.

6. The pen needle according to claim 1, further comprising
   at least one rib formed on a radially inward surface of the outer cover engaging the hub and positioning the hub within the outer cover.

7. The pen needle according to claim 1, wherein the hub is received in the outer cover with an interference fit, so that the outer cover rotates in unison with the hub received within the outer cover when the hub is installed on the medication pen, and the outer cover rotates with respect to the hub after the hub is fully installed on the medication pen.

8. The pen needle according to claim 1, wherein the hub has threads on an internal surface of the open proximal end of the hub receiving a threaded opening on a medication pen body.

9. The pen needle according to claim 1, wherein the hub has a flat distal patient-facing surface and a needle bearing post recessed proximally of the flat patient facing surface.

10. The pen needle according to claim 1, wherein the finger hold has a plurality of ribs formed on the gently concave sides.

11. The pen needle according to claim 1, wherein the flap is releasably held in the first closed position against the resistance of a camming surface.

12. The pen needle according to claim 1, wherein at least a portion of the flap projects outwardly beyond an outer periphery of the outer cover in at least one of the first and second closed positions.

13. The pen needle according to claim 1, wherein at least a portion of the flap projects outwardly beyond an outer periphery of the outer cover in both of the first and second closed positions.

* * * * *

UNITED STATES PATENT AND TRADEMARK OFFICE
CERTIFICATE OF CORRECTION

PATENT NO. : 10,661,025 B2
APPLICATION NO. : 15/100279
DATED : May 26, 2020
INVENTOR(S) : Sean Sullivan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 678 days.

Signed and Sealed this
Twentieth Day of December, 2022

*Katherine Kelly Vidal*
Katherine Kelly Vidal
*Director of the United States Patent and Trademark Office*